(12) United States Patent
Kelly et al.

(10) Patent No.: US 9,849,294 B2
(45) Date of Patent: Dec. 26, 2017

(54) SYSTEMS AND METHODS FOR CONTROLLING RATE RESPONSIVE PACING

(75) Inventors: Jonathan H. Kelly, Woodbury, MN (US); James Kalgren, Lino Lakes, MN (US); David L. Perschbacher, Coon Rapids, MN (US); James O. Gilkerson, Stillwater, MN (US); Les N. Peterson, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1879 days.

(21) Appl. No.: 12/537,362

(22) Filed: Aug. 7, 2009

(65) Prior Publication Data

US 2010/0036448 A1 Feb. 11, 2010

Related U.S. Application Data

(60) Provisional application No. 61/087,907, filed on Aug. 11, 2008.

(51) Int. Cl.
*A61N 1/00* (2006.01)
*A61N 1/372* (2006.01)
*A61N 1/365* (2006.01)

(52) U.S. Cl.
CPC ..... *A61N 1/37247* (2013.01); *A61N 1/36514* (2013.01); *A61N 1/36542* (2013.01)

(58) Field of Classification Search
CPC .... A61N 1/362; A61N 1/365; A61N 1/36542; A61N 1/37211; A61N 1/37217; A61N 1/37235; A61N 1/37247; A61N 1/37252; A61N 1/37264; A61B 5/0002; A61B 5/0006; A61B 5/02; A61B 5/024; A61B 5/044; A61B 5/742; A61B 5/7425; A61B 5/748; A61B 5/7485; G06F 3/01; G06F 15/0225; G06F 19/30
USPC .......... 128/903; 607/7, 9, 11, 15, 17, 18, 28, 607/30–32
See application file for complete search history.

(56) References Cited

U.S. PATENT DOCUMENTS 5,697,956 A * 12/1997 Bornzin ................... 607/28
5,713,937 A    2/1998 Nappholz et al.
5,844,572 A * 12/1998 Schott ................... 345/440
(Continued)

OTHER PUBLICATIONS

"Zoom® Latitude® Programming System, Model 3120," Jun. 27, 2007, 52 pages.
(Continued)

*Primary Examiner* — Nadia A Mahmood
(74) *Attorney, Agent, or Firm* — Pauly, DeVries, Smith & Deffner LLC

(57) ABSTRACT

Embodiments of the invention are related to medical systems and methods that can be used to control features of implanted medical devices, amongst other things. In an embodiment, the invention includes a medical system including an external medical device. The external medical device including a video output and a processor in communication with the video output. The system can be configured to display information through the video output as a graph, the graph comprising data representing pacing rates of an implantable device as a function of activity level over time. The system can further be configured to accept user input through direct manipulation of the graph. Other embodiments are also included herein.

15 Claims, 11 Drawing Sheets

(56) References Cited

U.S. PATENT DOCUMENTS

| | | | |
|---|---|---|---|
| 6,076,015 A * | 6/2000 | Hartley et al. | 607/20 |
| 6,237,398 B1 | 5/2001 | Porat et al. | |
| 6,665,558 B2 * | 12/2003 | Kalgren et al. | 600/510 |
| 6,937,900 B1 | 8/2005 | Pianca et al. | |
| 6,978,182 B2 | 12/2005 | Mazar et al. | |
| 7,218,968 B2 | 5/2007 | Condie et al. | |
| 2002/0151938 A1 * | 10/2002 | Corbucci | 607/25 |
| 2007/0270675 A1 | 11/2007 | Kane et al. | |
| 2008/0269843 A1 * | 10/2008 | Gerber et al. | 607/62 |

OTHER PUBLICATIONS

"Guidant Announces Market Launch of Wireless Heart Failure Device System," Oct. 31, 2005, http://news.bostonscientific.com/index.php?s=24913&item=22175, 4 pages.

"Model 3120 Zoom(R) Latitude(R) Programmer Maintenance, Apr. 2, 2008, 1 page".

* cited by examiner

SYSTEMS AND METHODS FOR CONTROLLING RATE RESPONSIVE PACING

This application claims the benefit of U.S. Provisional Application No. 61/087,907, filed Aug. 11, 2008, the contents of which are herein incorporated by reference.

TECHNICAL FIELD

This disclosure relates generally to medical systems and, more particularly, to medical systems that can be used to control features of implanted medical devices, amongst other things.

BACKGROUND OF THE INVENTION

Implantable medical devices can be used to provide pacing therapy to patients who have cardiac rhythm problems. For example, an implanted medical device can be used to provide pacing therapy to a patient with sinus node dysfunction, where the heart fails to properly initiate depolarization waves, or an atrio-ventricular conduction disturbance, where the conduction of depolarization waves through the heart tissue is impaired.

Implanted medical devices with pacing functionality, such as a pacemaker, typically deliver a pacing pulse of electricity to the heart in order to produce a heartbeat at the correct time. The implanted medical device includes electronic circuitry that is contained within a hermetically sealed enclosure that is sometimes referred to as a pulse generator. The pulse generators and associated electronics are implanted in the patient's chest and one or more leads are routed from the pulse generator, through the patient's vasculature, and to the patient's heart tissue. Electrical pulses are delivered through the leads to the heart tissue, initiating contraction of the heart.

One issue associated with cardiac pacing therapy is the need to adapt the pacing rate in response to the changing metabolic demands of the patient. For example, while a patient is sitting, sleeping, or otherwise being sedentary, the patient's cardiac output requirements are relatively low. However, when engaged in physical activity, a patient's cardiac output requirements increase in order to transport more oxygen to, and carbon dioxide from, various body tissues. The greater the intensity of the physical activity, the greater the cardiac output required to sustain the activity.

Methods have been devised for adapting cardiac pacing rates in response to exercise or exertion, referred to as "adaptive rate pacing" or "rate adaptive pacing". These methods generally depend on measuring something that serves as an index of exertion and then adjusting the pacing rate in response to changes in the measured quantity. In many cases, some type of algorithm is used to calculate a pacing rate based on exertion data as input. The algorithm may include various rate response parameters to control aspects of how the pacing rate is actually set.

SUMMARY OF THE INVENTION

Embodiments of the invention are related to medical systems and methods that can be used to control features of implanted medical devices, amongst other things. In an embodiment, the invention includes a medical system including an external medical device. The external medical device can include a video output and a processor in communication with the video output. The system can be configured to display information through the video output as a graph, the graph comprising data representing pacing rates of an implantable device as a function of activity level over time. The system can further be configured to accept user input through direct manipulation of the graph.

In an embodiment, the invention includes a method of operating a medical device. The method can include providing an image on a graphical display, including providing a graph of historical pacing rate of an implantable medical device over time. The method can further include receiving user input through direct manipulation of the graph by the user. The method can further include calculating changes to parameters of a pacing rate algorithm in response to the user input. The method can further include providing a graph of a projected pacing rate of the implantable medical device over time based on the calculated changes to the parameters of the pacing rate algorithm.

In an embodiment, the invention includes a device. The device can include a graphical display and a machine-readable medium comprising instructions. The instructions, when implemented by one or more processors, can perform the following operations providing an image on a graphical display, including providing a graph of historical pacing rate of an implantable medical device over time, receiving user input through direct manipulation of the graph by the user, calculating changes to parameters of a pacing rate algorithm in response to the user input, and providing a graph of a projected pacing rate of the implantable medical device over time based on the calculated changes to the parameters of the pacing rate algorithm.

In an embodiment, the invention can include a medical system including a video output and a processor in communication with the video output. The system configured to display a user interface comprising a series of options affecting pacing rate response, wherein the clinical effects on pacing rate of each of the options within the series are displayed through the user interface in a textual format. The system can be further configured to accept user input through user selection of one or more of the series of options. The processor can be configured to calculate changes to the parameters of a pacing rate algorithm in response to the user input.

In an embodiment, the invention can include a method of operating a medical device including providing an image on a graphical display, including providing a graph of historical pacing rate of an implantable medical device over time, receiving user input in response to a series of options regarding desired clinical effects of pacing behavior of the implantable medical device, calculating changes to the parameters of a pacing rate algorithm in response to the user input, and providing a graph of a projected pacing rate of the implantable medical device over time based on the calculated changes to the parameters of the pacing rate algorithm.

In an embodiment, the invention can include a medical system including an implantable medical device and an external device in communication with the implantable medical device. The external device can be configured to program rate response parameters of the implantable medical device. The external device can include a video output and a processor in communication with the video output. The system can be configured to display information through the video output as a graph, the graph comprising data representing pacing rates of the implantable medical device as a function of activity level over time. The system can further be configured to accept user input through direct manipulation of the graph.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

Figure 1:
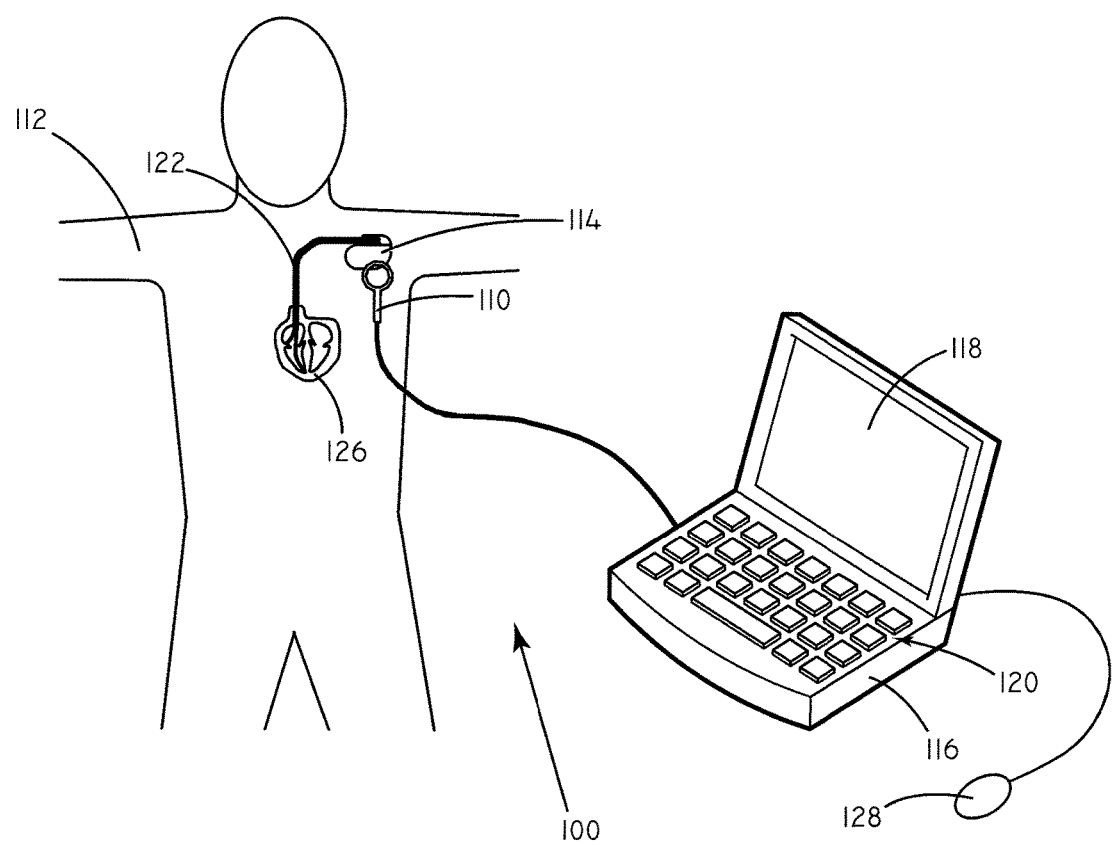
FIG. 1 is a schematic diagram of an exemplary implementation, consistent with at least one embodiment of the invention.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Implantable devices including rate adaptive pacing technology can provide significant clinical benefits because cardiac output can be increased through more rapid pacing in order to meet greater metabolic needs for oxygen brought on by physical activity. Various algorithms have been developed over time in order to provide rate adaptive pacing. The input to these algorithms includes data regarding activity levels of a patient over time. The output of these algorithms is a pacing rate. However, a desirable pacing rate for one patient may be different than a desirable pacing rate for another patient, even where activity levels are the same. As such, the algorithms generally include one or more parameters ("rate response parameters") that can be adjusted in order to tune the rate adaptive pacing response according to the needs of individual patients.

Manipulation of the rate response parameters is typically done by a clinician using an external device such as a programmer/recorder/monitor device to program the implantable pacing device. Exemplary rate response parameters can include an activity threshold, a reaction time, a response factor, and a recovery time, though it will be appreciated that other rate response parameters can also be used and that those provided here are only exemplary. The activity threshold parameter specifies the noise floor for data from activity level sensors. The reaction time parameter specifies the amount of time that will pass before the system increases pacing rate in response to activity level sensor data that indicates increased physical activity. The response factor parameter specifies a gain factor for pacing rate in response to activity level sensor data. The recovery time parameter specifies the amount of time that will pass before the system decreases pacing rate in response to activity level sensor data that indicates decreased physical activity. The rate response parameters can be changed according to the desires of the clinician responsible for the patient.

In some scenarios the physician may look at historical data regarding how the device has varied pacing rates over time in response to varying levels of physical activity. In some cases, the historical pacing rate data may be displayed as a graph. Seeing this data, they may have ideas regarding how they think the pacing response should be changed in order to benefit the patient. Unfortunately, with many existing systems, they must manipulate individual rate response parameters in order to implement desired changes. In other words, even though the clinician may have an idea regarding how they would like the graph of pacing rate data to be changed, they must go through the sometimes arduous process of tinkering with individual rate response parameters in order to try to achieve the desired result.

Embodiments included herein can facilitate programming of a rate adaptive pacing response of an implantable device. In various embodiments, a clinician can provide input regarding rate response parameters through direct manipulation of a graph of pacing rates over time, thereby enhancing usability of the system. In an embodiment, the invention includes a medical system including a video output and a processor in communication with the video output. The system can be configured to display information through the video output as a graph, the graph comprising data representing pacing rates of an implantable device as a function of activity level over time. The system can further be configured to accept user input through direct manipulation of the graph.

Frequently, clinicians have a desired clinical result in mind when they approach the programming task. For example, a patient may complain of lacking energy when engaging in physical activity and so the clinician may determine that the programming needs to be adjusted so that the implantable device paces more rapidly when the patient undergoes physical activity. However, in order to achieve the desired clinical result with many systems, they must generally try to determine how the rate response parameters need to be changed and then make the changes to each rate response parameter individually. This process decreases the usability of the system. Confusion can also result where the clinician is unsure of the effects of individual rate response parameters. This is particularly true where more than one of the individual rate response parameters must be changed in order to achieve a desired clinical result.

In various embodiments, user interface features such as buttons can be included that include descriptions which describe clinically relevant effects to be achieved. When such a button is actuated, the system can then automatically determine how to change individual rate response parameters is order to achieve the desired clinical result. In an embodiment, the invention includes a medical system comprising a video output and a processor in communication with the video output. The system can be configured to display a user interface comprising a series of options affecting pacing rate response, wherein the clinical effects on pacing rate of each of the options within the series are displayed through the user interface in a textual format. The system further can be configured to accept user input through user selection of one or more of the series of options. The processor can be configured to calculate changes to the parameters of a pacing rate algorithm in response to the user input.

FIG. 1 is a schematic of an exemplary system 100, consistent with at least one embodiment of the invention. The system 100 can include an implantable medical device 114 disposed within a patient 112. The implantable medical device 114 can include pacing functionality. The implantable medical device 114 can be of various types such as, for example, a pacemaker, a cardioverter-defibrillator, a cardiac resynchronization device, or the like. In some embodiments, the implantable medical device 114 can include one or more leads 122 disposed in or near the patient's heart 126.

The implantable medical device 114 can be in communication with an external medical device 116. In some embodiments, communication between the implantable medical device 114 and the external medical device 116 can be via inductive communication through a wand 110 held on the outside of the patient 112 near the implantable medical device 114. However, in other embodiments, communication can be carried out via radiofrequency transmission, acoustically, or the like.

The implantable medical device 114 can include one or more implantable sensors in order to gather data regarding the patient 112. For example, the implantable medical device 114 can include an activity level sensor. Exemplary activity level sensors are described in greater detail below.

The implantable medical device 114 can be configured to store data over a period of time, and periodically communicate with the external medical device 116 in order to transmit some or all of the stored data.

The external medical system 116 can be for example, a programmer/recorder/monitor device, a computer, an advanced patient management system, a personal digital assistant (PDA), or the like. Exemplary programmer/recorder/monitor devices include the Model 3120 Programmer, available from Boston Scientific Corporation, Natick, Mass. The external medical device 116 can include a user input device, such as a keyboard 120 and/or a mouse 128. The external medical device 116 can include a video output channel and video output device, such as a video display 118 for displaying video output. The displayed video output can include a user interface screen.

The external medical system 116 can display real-time data and/or stored data graphically, such as in charts or graphs, and textually through the user interface screen. In particular, the external medical system 116 can be configured to display a graph including data that represents pacing rates of the implantable medical device 114 as a function of activity level over time.

Figure 2:
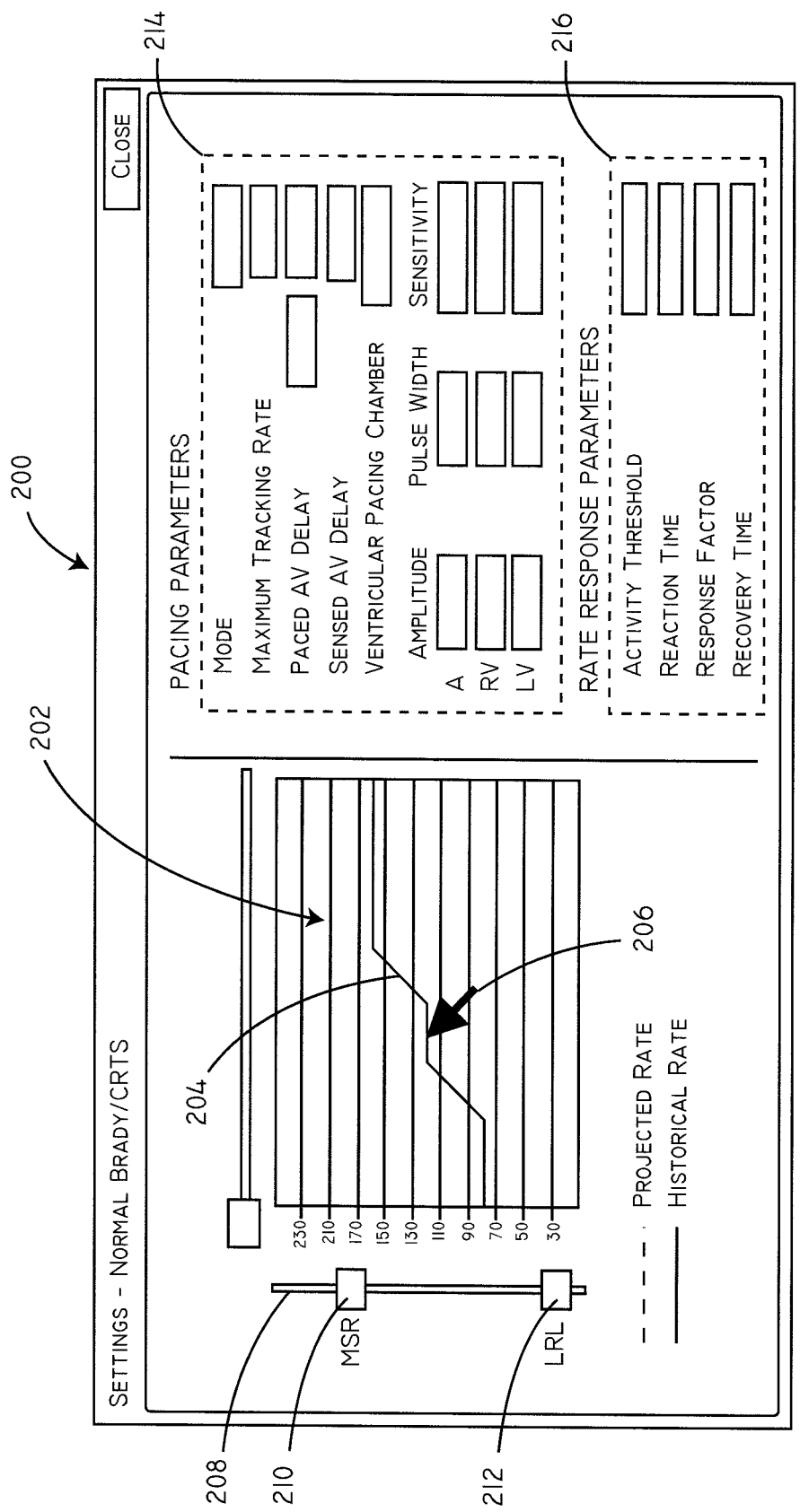
FIG. 2 is a schematic illustration of a user interface screen in accordance with various embodiments herein.

Referring now to FIG. 2, a schematic illustration of a user interface screen 200 in accordance with various embodiments herein is shown. The user interface screen 200 can include a graph 202 that includes data regarding pacing rates over time. The data can be displayed in the form of a line 204. However, in other embodiments the data can be displayed in other ways such as a series of points. In the view shown in FIG. 2, the line 204 represents historical pacing rate data. Historical pacing rate data reflects actual pacing rates of the implantable over a past period of time. For example, the historical pacing rate data can reflect actual pacing rates over a period of time prior to an office visit with the clinician. Alternatively, the historical pacing rate data can reflect actual pacing rates recorded during the office visit during a physical activity test, such as actual pacing rates observed while having the patient walk up stairs. While not shown in the graph 202 in this embodiment, data generated by a physical activity sensor (historical activity level data) is also tracked by the system for the period of time of the historical pacing rate data.

The user interface screen 200 can also include textual data regarding pacing parameters 214 and textual data regarding rate response parameters 216. In addition, the user interface screen 200 can include controls such as a slider bar 208 in order to control various other pacing parameters such as a maximum pacing rate in response to sensor data ("MSR") and a lower pacing rate limit ("LRL"). For example, the MSR can be controlled by moving a first button 210 on the slider bar 208 and the LRL can be controlled by moving a second button 212 on the slider bar 208.

A system user, such as a clinician, can directly interface with the data displayed in the graph 202. By way of example, the system user can use a cursor icon 206 as controlled by a mouse, stylus, touch control, or the like, in order to directly interface with the data in the graph 202. The user can provide user input regarding desired changes to the way in which the device paces based on the set of historical activity level data. For example, if the system user desires that a faster pacing rate be reached by the implantable device, the user can use the cursor icon and click on the line 204 and drag it upward. In some embodiments, an individual point in the graph can be dragged without disturbing adjacent points. In other embodiments, portions of a line surrounding a selected point can be dragged along with the selected point. In some embodiments, the user can directly interface with the graph by clicking, double clicking, dragging, highlighting, or the like.

After the user provides input, the system can calculate appropriate values for the rate response parameters that will cause the implanted device to pace at rates that correspond to the user input. Techniques for performing such calculations are described in greater detail below.

Figure 3:
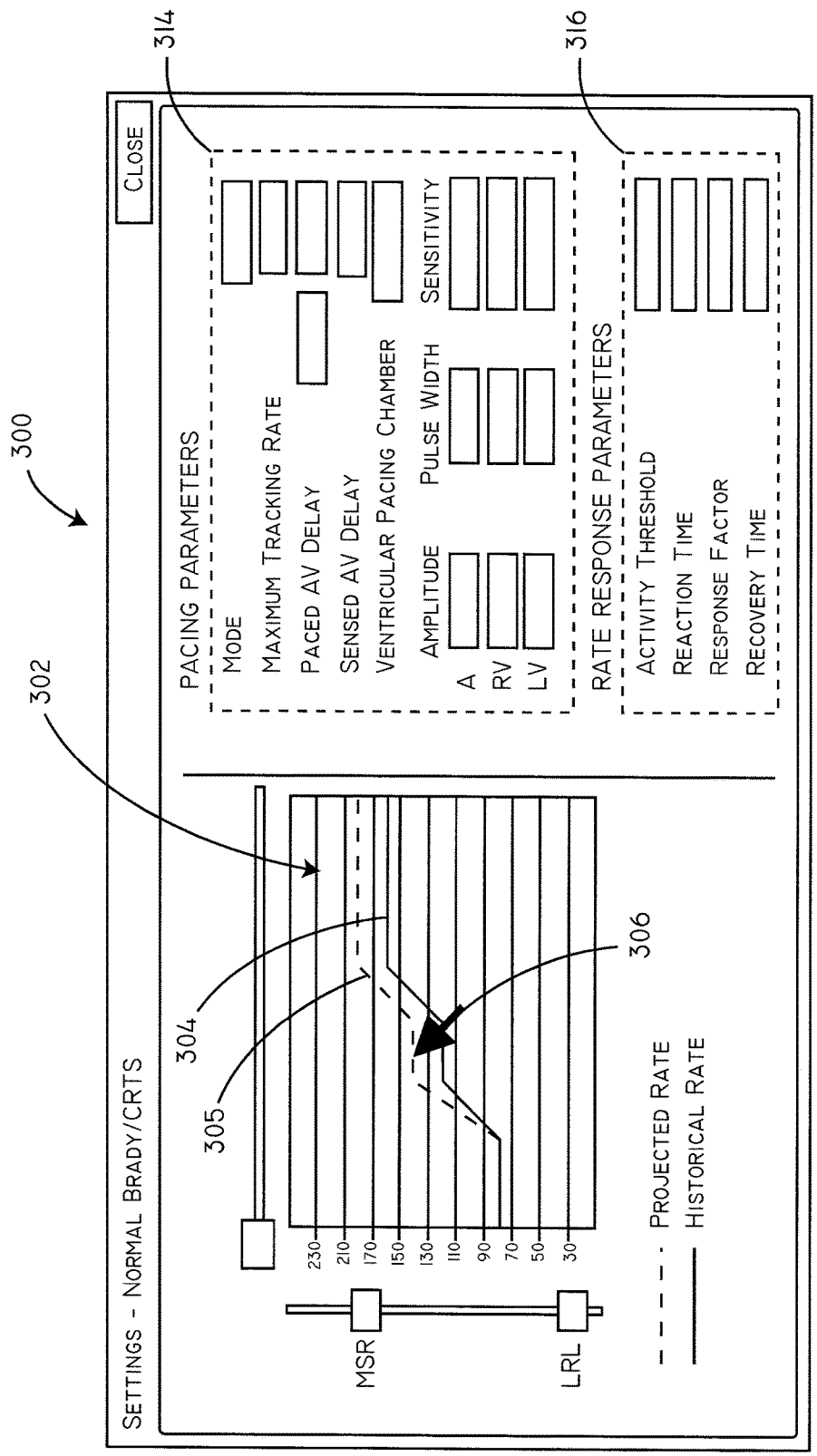
FIG. 3 is a schematic illustration of a user interface screen in accordance with various embodiments herein.

Referring now to FIG. 3, a schematic illustration of a user interface screen 300 in accordance with various embodiments herein. In this view, the user interface screen 300 again shows textual data regarding pacing parameters 314 and textual data regarding rate response parameters 316. The user interface screen 300 also shows a graph 302 that includes data regarding pacing rates over time. In this view, a first line 304 represents historical pacing rate data while a second line 305 represents projected pacing rate data.

The projected pacing rate data has been generated in response to user input provided through direct manipulation of the graph, such as through using a cursor icon 306 to select and move portions of the data displayed in the graph. As described above, after the user provides such input, the system can calculate appropriate new values for the rate response parameters that will cause the implanted device to pace at rates that correspond to the user input. The system can then use the historical activity level data along with the new calculated values for rate response parameters in order to generate a projection of the rate the implantable device would have paced at, if the new rate response parameter values were actually in place during the period in which the historical activity level data was recorded. In the view shown in FIG. 3, the system user has selected a portion of the first line 304, representing historical pacing rate data, and moved it upwards indicating a desire to have faster pacing rates. In response, the system has calculated a new set of values for the rate response parameters to accommodate this desire. Then the system has generated a second line 305, representing projected pacing rate data, to indicate to the user how the pacing rates would have been differed based on the same historical activity level data, were the new values for the rate response parameters in effect during the period in which the historical activity level data was recorded.

In some embodiments, the old values, new values, and/or calculated changes in the rate response parameters 316 can be shown in the user interface screen 300.

Figure 4:
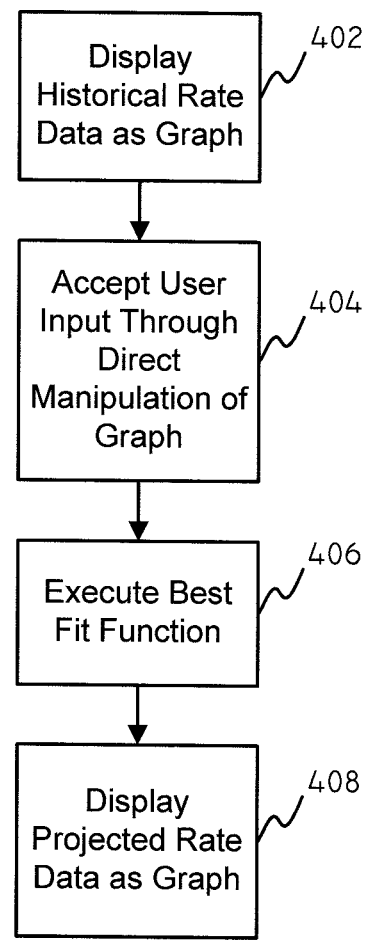
FIG. 4 is a flowchart illustrating a method by which the system can receive user input and display data regarding pacing rates.

Referring now to FIG. 4, a flowchart is shown illustrating a method by which the system can receive user input and display data regarding pacing rates. In a first operation 402, the system can be configured to display historical pacing rate data as a graph. For example, actual historical pacing rates can be displayed as they occurred over time. In a second operation 404, the system can be configured to accept user input through direct manipulation of the graph of the historical pacing rate data. In a third operation 406, the system can be configured to calculate how the rate response parameters need to be changed in order to cause the implantable device to pace according to the user input. For example, the system can execute a best fit function in order to calculate how the rate response parameters should be changed. In a fourth operation 408, the system can be configured to display the projected rate data as a graph. The projected rate data can be calculated based on the new values for the rate response parameters and the historical activity sensor data. In some embodiments, the both the historical pacing rate data and the projected pacing rate data can be displayed as part of a graph at the same time. In other embodiments, only one or the other is displayed and they are not displayed simultaneously.

It will be appreciated that there are many ways of performing a best fit function to determine the set of rate response parameter values that produces a line or curve that most closely matches a set of data representing desired pacing rates. For example, in one approach the system can systemically vary the values of individual rate response parameters and then calculate pacing rates based on the historical activity level data producing, in effect, a series of lines or curves representing possible ways in which the pacing behavior of the device can be changed based on changes to the given set of rate response parameters. The system can then determine which of the possible lines is the closest match to the desired pacing rates through linear or non-linear regression techniques, amongst other approaches. The set of rate response parameter values used to create the closest matching line or curve would then be the new values that the system could use to program the implantable device.

In some cases it may not be possible to change the rate response parameters in a way such that the pacing rate of the implantable device is exactly as the user specifies through manipulation of the graph. In other words, since there are a limited number of rate response parameters, it may not be possible to make changes to them in a manner so that the desired result is precisely achieved. As such, in some embodiments, the system can include a user interface that displays a historical pacing rate, a desired pacing rate, and a projected pacing rate.

Figure 5:
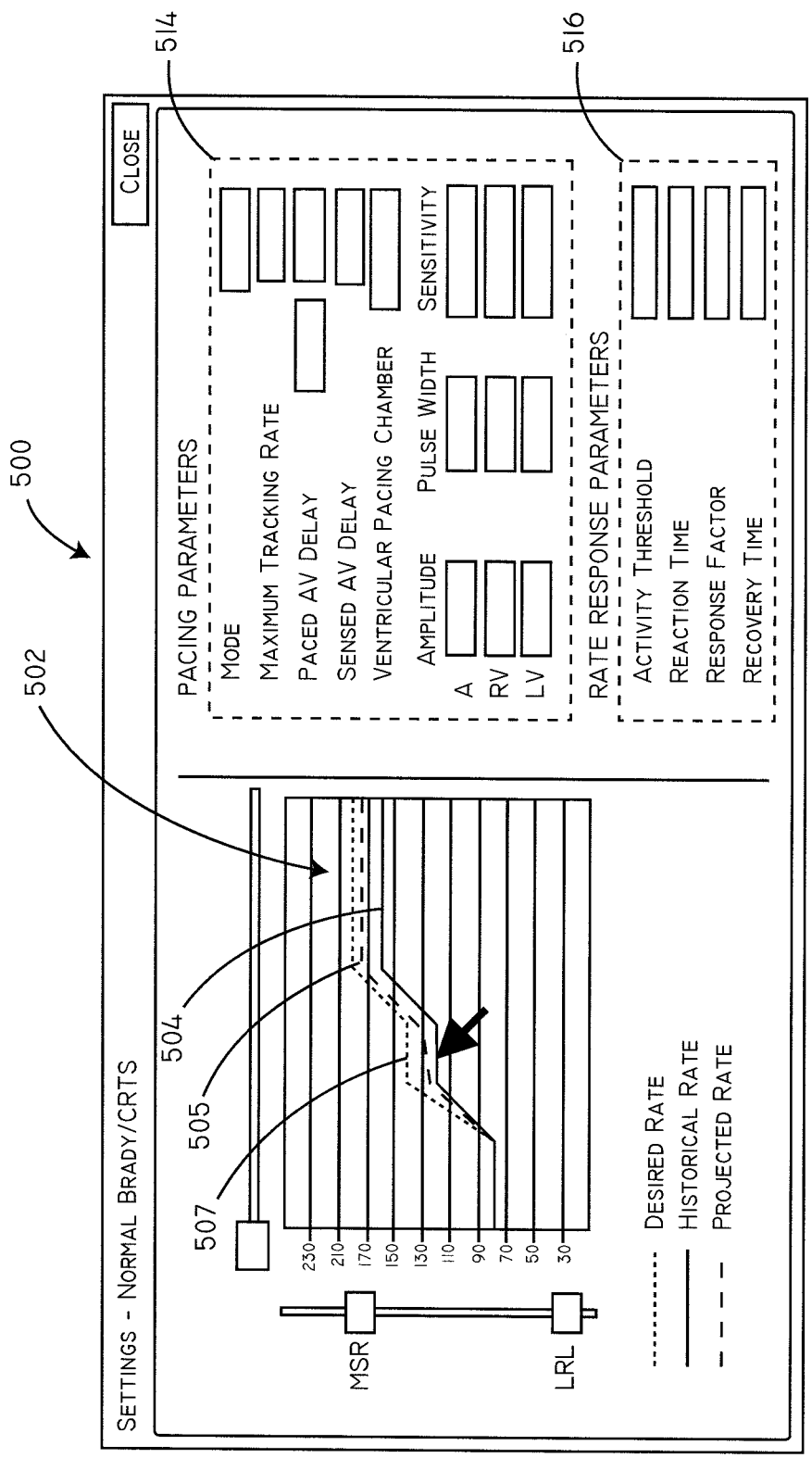
FIG. 5 is a schematic illustration of a user interface screen in accordance with various embodiments herein.

Referring now to FIG. 5, a schematic illustration of a user interface screen 500 in accordance with various embodiments herein. In this view, the user interface screen 500 again shows textual data regarding pacing parameters 514 and textual data regarding rate response parameters 516. The user interface screen 500 also shows a graph 502 that includes data regarding pacing rates over time. In this view, a first line 504 represents historical pacing rate data, a second line 505 represents projected pacing rate data, and a third line 507 represents desired pacing rate data. The desired pacing rate data is a reflection of the user input received. In other words, the desired pacing rate data represents a literal view of how the system user wants the pacing rate to look over time.

In contrast, the projected pacing rate data is based upon the desired pacing rate data, but takes into account what is actually possible based on manipulation of the set of rate response parameters 516 for the particular implanted device. For example, the projected pacing rate data can represent the results of a best fit function performed on the desired pacing rate data in view of the pacing rate parameters.

Figure 6:
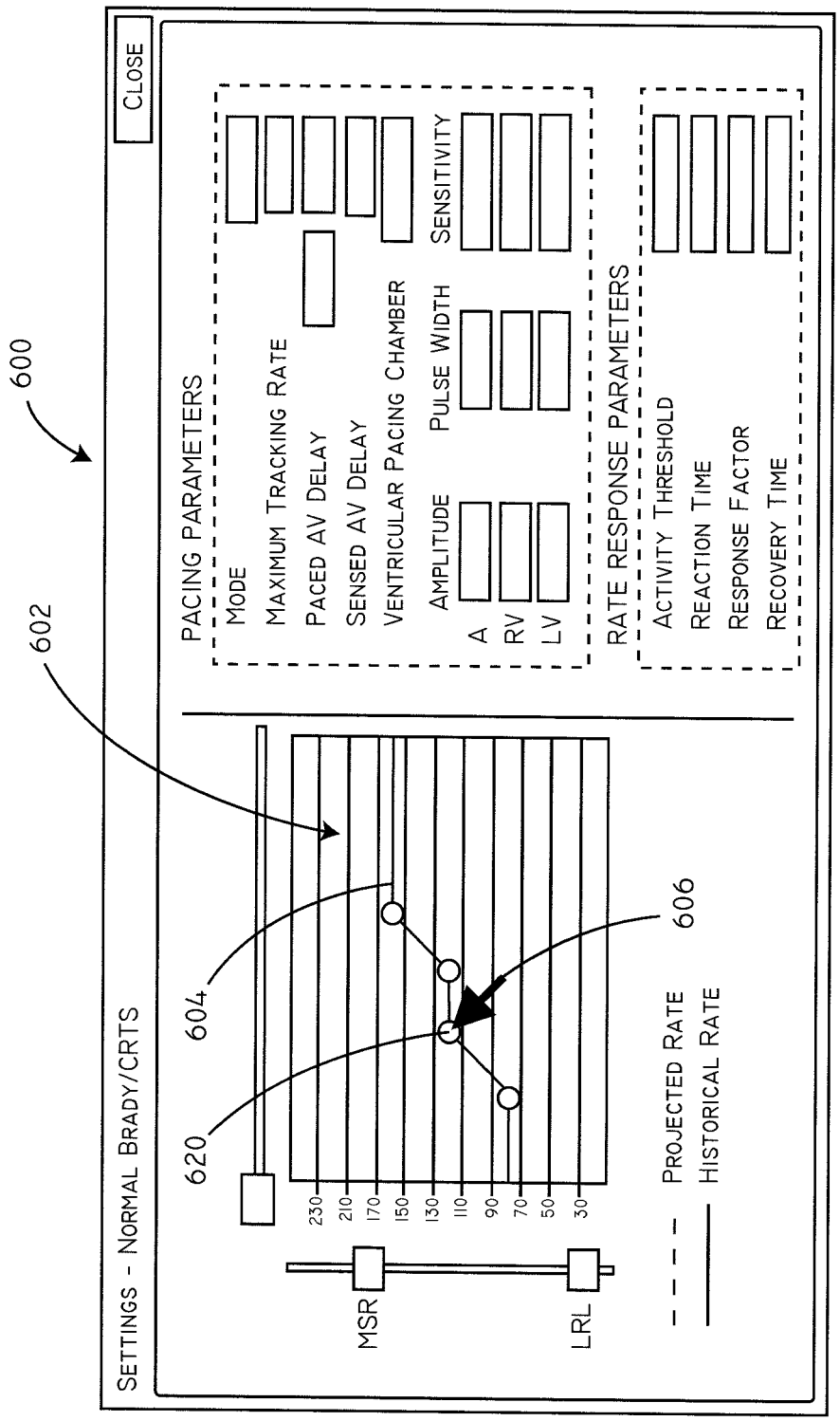
FIG. 6 is a schematic illustration of a user interface screen in accordance with various embodiments herein.

It will be appreciated that various other features can be included with the user interface in order to enhance usability. By way of example, the pacing rate data displayed in the graph can include features that enhance the ability of the user to directly manipulate the graph. Referring now to FIG. 6, a schematic illustration of a user interface screen 600 in accordance with various embodiments herein. The user interface screen 600 shows a graph 602 that includes data regarding pacing rates over time. In this view, a first line 604 represents historical pacing rate data. A series of manipulation elements 620 (displayed here as spheres) are superimposed over the first line 604. The manipulation elements 620 can serve as guideposts for the user in terms of discrete elements can be dragged and dropped by the user. For example, using a cursor icon 606, the system user can directly select one of the manipulation elements 620 and drag it into a desirable position. Then the system can perform other functions described herein such as calculating changes to pacing rate parameters and the like.

Figure 7:
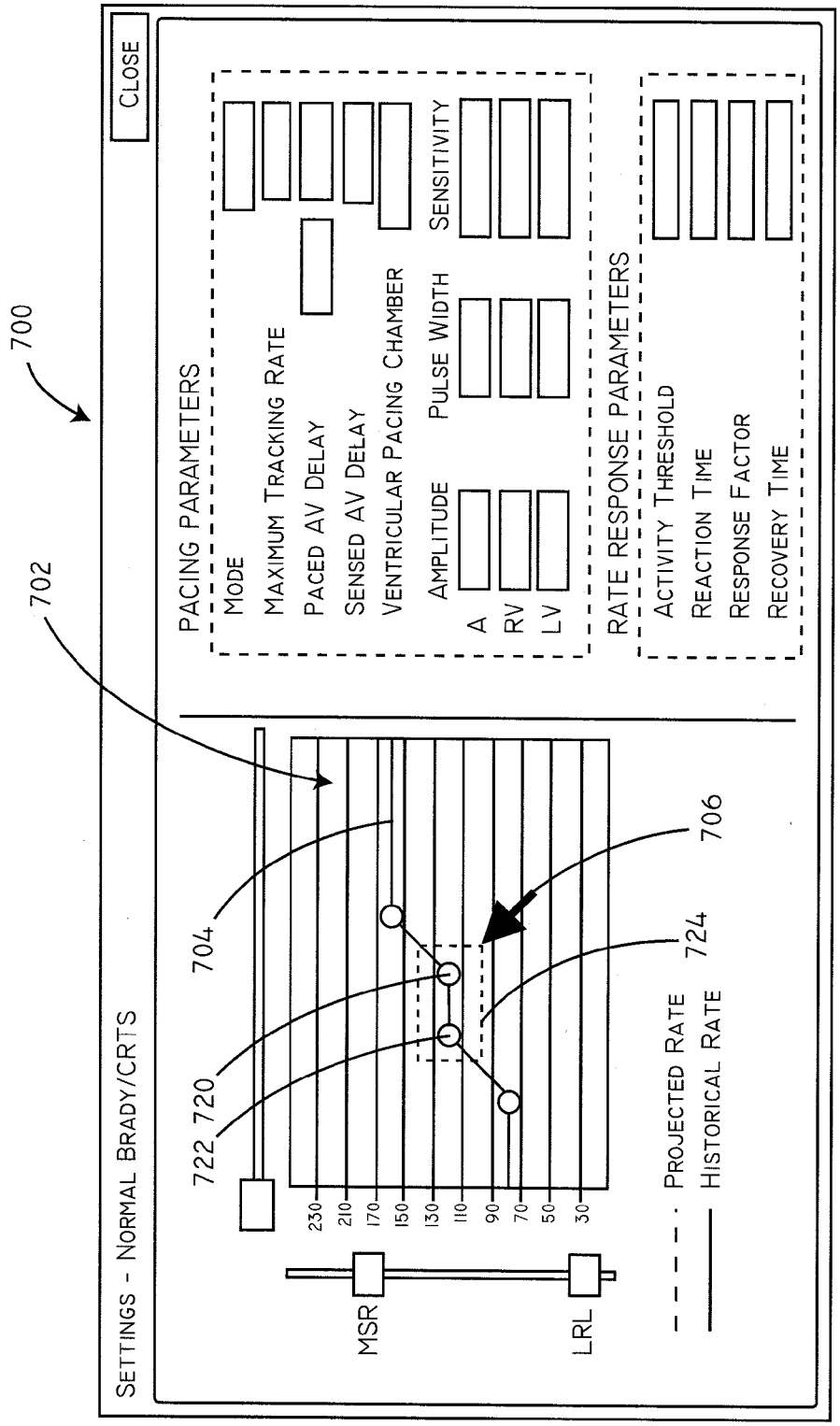
FIG. 7 is a schematic illustration of a user interface screen in accordance with various embodiments herein.

Other features can be included with the user interface so that the system user can make changes as efficiently as possible. For example, in various embodiments the user can select multiple points on the graph of pacing rate data so that multiple segments can be changed simultaneously. Referring now to FIG. 7, a schematic illustration of a user interface screen 700 in accordance with various embodiments herein. The user interface screen 700 shows a graph 702 that includes data regarding pacing rates over time. In this view, a first line 704 represents historical pacing rate data. A series of manipulation elements 720 and 722 are superimposed over the first line 704. In this embodiment, the system user can select both element 720 and element 722 for manipulation by using the cursor icon 706 to draw a box 724 around both manipulation elements.

Figure 8:
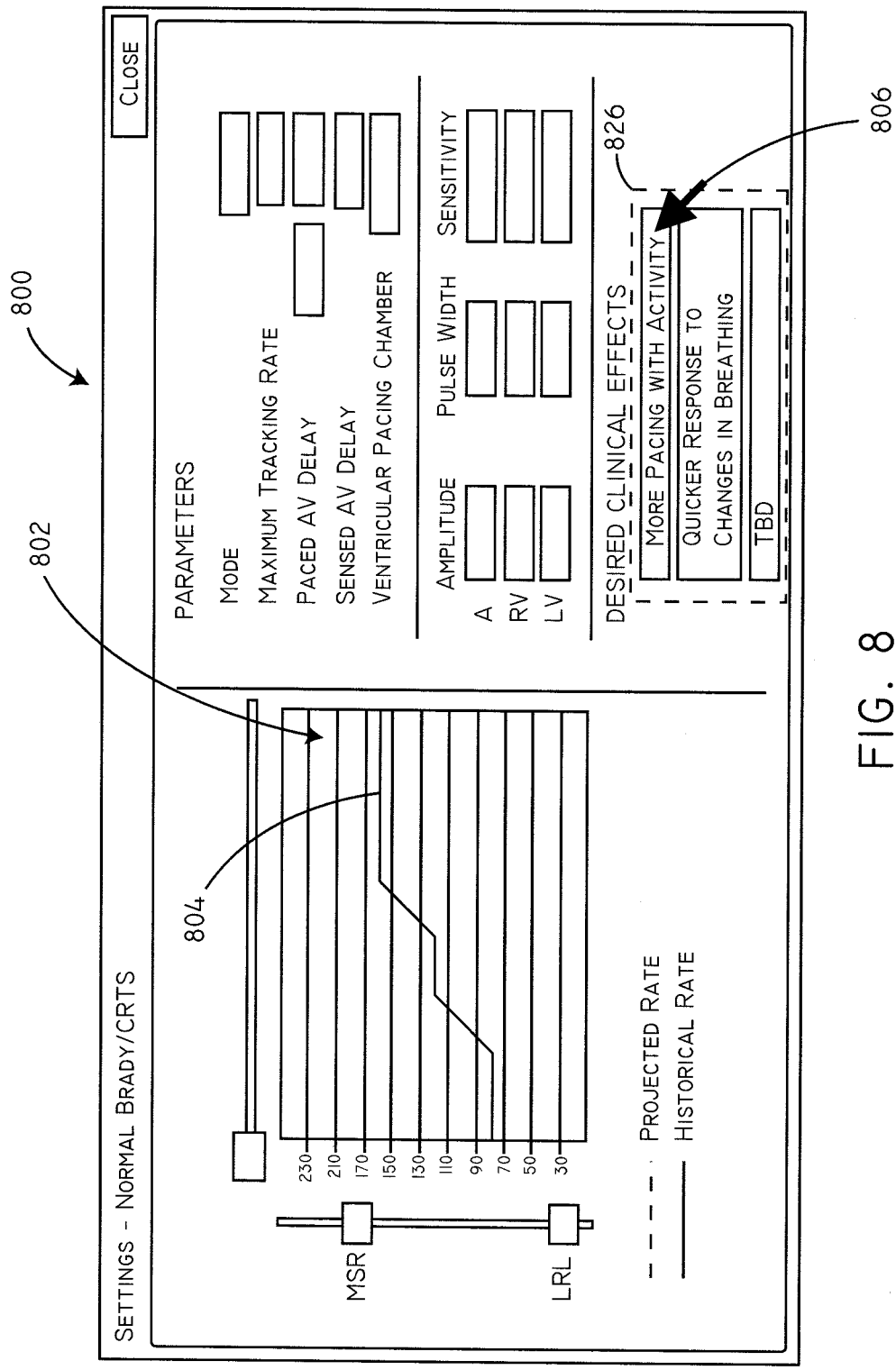
FIG. 8 is a schematic illustration of a user interface screen in accordance with various embodiments herein.

In various embodiments, user interface features such as buttons can be included that include descriptions which describe clinically relevant effects to be achieved. Referring now to FIG. 8, a schematic illustration of a user interface screen 800 in accordance with various embodiments herein. The user interface screen 800 shows a graph 802 that includes data regarding pacing rates over time. In this view, a first line 804 represents historical pacing rate data.

The user interface screen 800 also includes a series of options 826, shown here as a series of buttons, that a system user can select using a cursor icon 806. The series of options 826 can each include a clinically relevant textual description of a desired change to the pacing rate over time. Exemplary clinically relevant textual descriptions can include descriptions such as "more pacing with activity", "quicker response to changes in breathing", and the like. As such, the system user, generally having some type of clinical effect in mind, can look over the series of options 826 and find one that matches the effect they intend. The system user then provides input to the system by selecting one or more of the options and then the system can calculate changes to the pacing rate parameters. Though not shown in FIG. 8, in some embodiments, after calculating changes to the pacing rate parameters, the system can display data that represents projected pacing rates, similar to that shown in FIG. 3.

Figure 9:
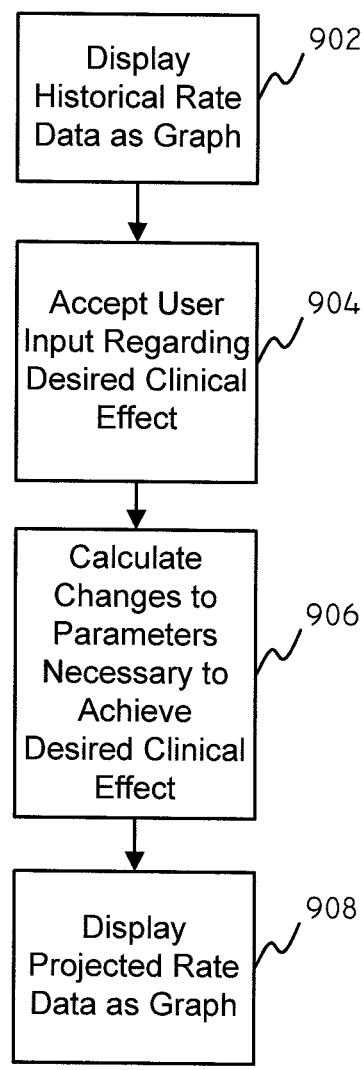
FIG. 9 is a flowchart illustrating a method by which the system can receive user input and implement changes to pacing rates.

Referring now to FIG. 9, a flowchart is shown illustrating a method by which the system can receive user input and implement changes to pacing rates. In a first operation 902, the system can be configured to display historical pacing rate data as a graph. For example, actual historical pacing rates can be displayed as they occurred over time. Optionally, this first operation may be omitted in some embodiments. In a second operation 904, the system can be configured to accept user input regarding a desired clinical effect through user actuation of screen elements, such as buttons, that include textual descriptions of clinical effects. In a third operation 906, the system can be configured to calculate how the rate response parameters need to be changed in order to cause the implantable device to pace according to the user input. For example, in some embodiments, a lookup table can contain information regarding how the rate response parameters should be changed in response to a particular button being pushed. In some cases, pushing of a particular button may result in only one rate response parameter being changed. In other embodiments, pushing of a particular button may result in multiple rate response parameters being changed. In a fourth operation 908, the system can be configured to display the projected rate data as a graph. The projected rate data is calculated based on the new values for the rate response parameters and the historical activity sensor data. Optionally, the fourth operation may be omitted in some embodiments.

Figure 10:
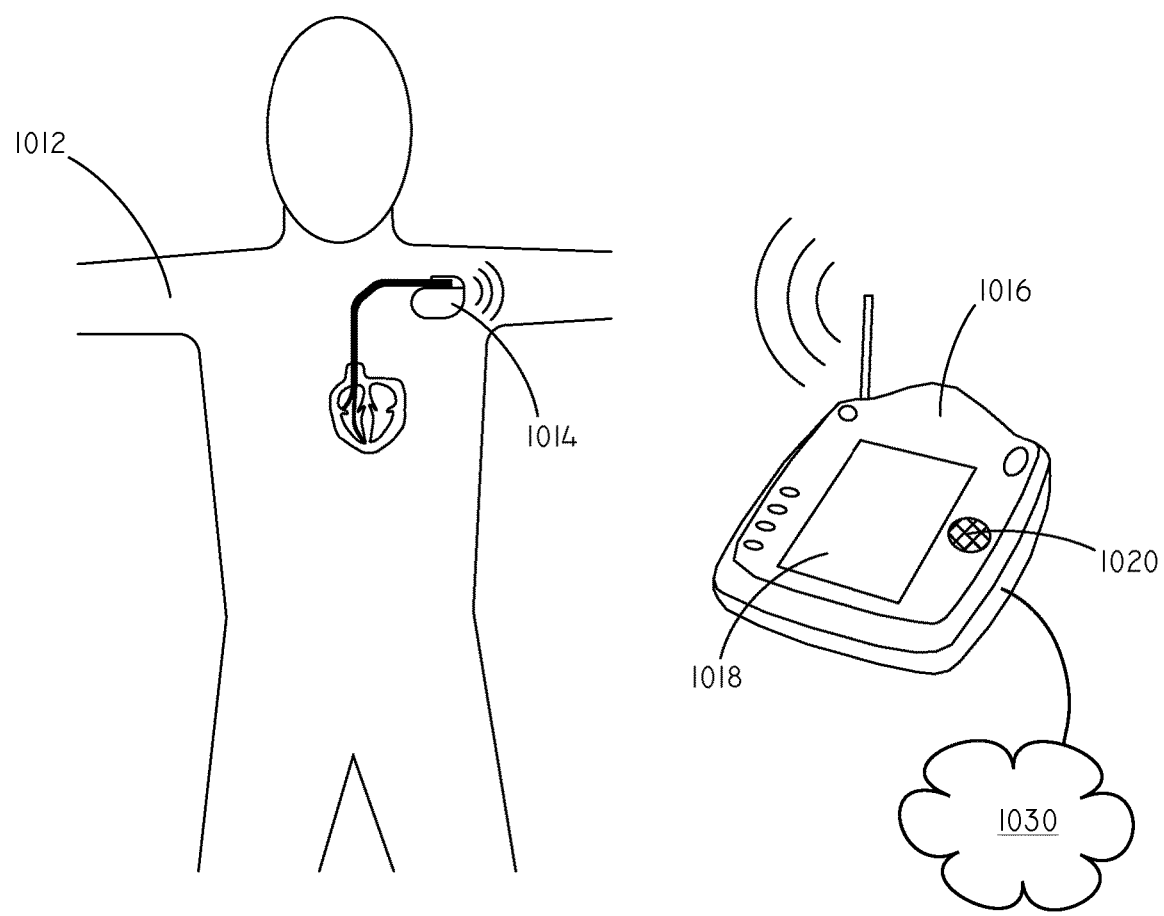
FIG. 10 is a schematic diagram of an implementation, in accordance with various embodiments.

It will be appreciated that the external device or medical system that can be used to display the user interface screen of various embodiments herein can take on many different forms. FIG. 10 is a schematic of an implementation, in accordance with various embodiments. An implantable device 1014, implanted within a patient 1012, is in communication with an external device 1016 that can have a video output in the form of a display screen 1018 and an audio output in the form of a speaker 1020. Communication can be through radio frequency, inductive transmission, acoustically, or any other means available.

The external device 1016 can be an in-home monitoring system for use by a patient in their home or residence. An exemplary in-home monitoring system is the LATITUDE® patient management system, available from Boston Scientific Corporation, Natick, Mass. Aspects of exemplary in-home monitoring systems are described in U.S. Pat. No. 6,978,182, the content of which is herein incorporated by reference in its entirety. In such a situation, the external device 1016 can be in communication with an additional processing device such as a workstation or server located remotely from the external device 1016 to enable access to the information by doctors or technicians. For example, the external device 1016 can be in communication with a workstation or server through the Internet 1030 or another type of data connection. In some embodiments, the external device can be a mobile device (not shown), such as a hand-held device or a device worn on a belt.

In some embodiments, the invention includes a device including a graphical display and a machine-readable medium comprising instructions. The instructions can perform various operations when implemented by one or more processors. By way of example, the operations can include those in accordance with methods as described herein. The machine-readable medium can include random access memory (RAM), read-only memory (ROM), magnetic data storage media, optical data storage media, flash memory and the like.

Figure 11:
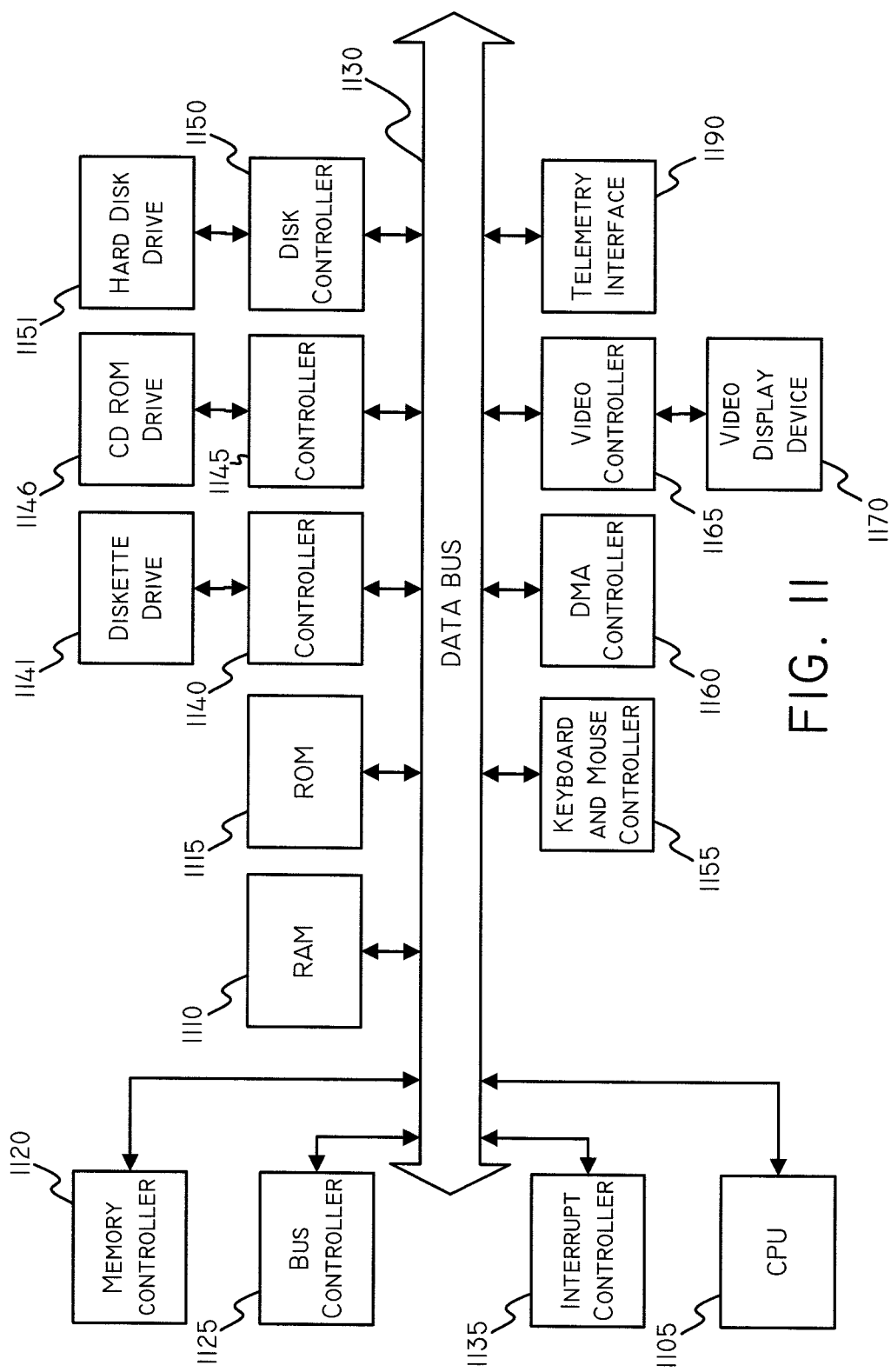
FIG. 11 is a schematic diagram of various components shown in accordance with some embodiments of the invention.

External devices to display information, such as programmer/recorder/monitors, can include components common to many computing devices. Referring now to FIG. 11, a diagram of various components is shown in accordance with some embodiments of the invention. The external system includes a central processing unit (CPU) 1105 or processor, which may include a conventional microprocessor, random access memory (RAM) 1110 for temporary storage of information, and read only memory (ROM) 1115 for permanent storage of information. A memory controller 1120 is provided for controlling system RAM 1110. A bus controller 1125 is provided for controlling data bus 1130, and an interrupt controller 1135 is used for receiving and processing various interrupt signals from the other system components.

Mass storage can be provided by diskette drive 1141, which is connected to bus 1130 by controller 1140, CD-ROM drive 1146, which is connected to bus 1130 by controller 1145, and hard disk drive 1151, which is connected to bus 1130 by controller 1150. User input to the programmer system may be provided by a number of devices. For example, a keyboard and mouse can connected to bus 1130 by keyboard and mouse controller 1155. DMA controller 1160 is provided for performing direct memory access to system RAM 1110. A visual display is generated by a video controller 1165 or video output, which controls video display 1170. The external system can also include a telemetry interface 1190 or telemetry circuit which allows the external system to interface and exchange data with an implantable medical device. It will be appreciated that some embodiments may lack various elements illustrated in FIG. 11.

Activity Level Sensors and Sensor Data

Various embodiments of systems and methods herein may utilize data from activity level sensors in conjunction with displaying pacing rate data and calculating projected pacing rates, amongst other things. Exemplary activity level sensors can include impedance sensors, pressure sensors, accelerometers, chemical sensors, flow meters, temperature sensors, and the like. Such sensors can produce data that are directly or indirectly correlated to physical exertion such that the data can be used to track changes in physical exertion. Impedance can be sensed between various electrodes of implantable medical device systems. Exemplary pressure sensors are described in U.S. Pat. No. 6,237,398, herein incorporated by reference in its entirety. In still other embodiments, the sensor can be an accelerometer. Exemplary accelerometers are described in U.S. Pat. No. 6,937,900, herein incorporated by reference in its entirety. In some embodiments, the sensor can be a chemical sensor. Exemplary chemical sensors are described in U.S. Publ. Pat. App. No. 2007/0270675, herein incorporated by reference in its entirety.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A medical system comprising:
    an external medical device comprising
        a video output; and
        a processor in communication with the video output; and
    an implantable medical device capable of rate adaptive pacing based on a pacing algorithm, wherein the pacing algorithm includes one or more rate response parameters,
        the external medical device configured to display information through the video output as a graph, the graph comprising data representing pacing rates of the implantable medical device as a function of activity level over time; the external medical device further configured to accept pacing rate user input through direct manipulation of the graph, wherein the system is configured to calculate changes to one or more rate response parameters of the pacing algorithm in response to pacing rate user input.

2. The medical system of claim 1, wherein the graph comprises a first set of data, the first set of data comprising historical pacing rates as a function of historical activity level data over time.

3. The medical system of claim 2, wherein the first set of data is displayed as a graphical object.

4. The medical system of claim 2, wherein the graphical object comprises a line.

5. The medical system of claim 1, wherein the graph comprises a second set of data, the second set of data comprising projected pacing rates as a function of historical activity level data over time.

6. The medical system of claim 5, wherein the set of values for rate response parameters of the pacing algorithm based on the user input results in the projected pacing rates.

7. The medical system of claim 6, wherein the external device is configured to program the set of values for rate response parameters into the implantable medical device.

8. The medical system of claim 6, wherein calculating a set of values comprises executing a best fit function.

9. The medical system of claim 6, further comprising displaying the set of values through the video output.

10. The medical system of claim 1, wherein the graph comprises a third set of data, the third set of data comprising desired pacing rates as a function of historical activity level data over time.

11. The medical system of claim 10, wherein the third set of data is generated in response to the user input.

12. The medical system of claim 10, wherein the set of values for rate response parameters of the pacing algorithm result in pacing that approximates the desired pacing rates as a function of historical activity level data over time.

13. The medical system of claim 12, wherein the rate response parameters are selected from the group consisting of an activity threshold, a reaction time, a response factor, and a recovery time.

14. The medical system of claim 1, wherein the activity level data comprises data gathered by an implantable sensor.

15. The medical system of claim 1, wherein the activity level data comprises data selected from the group consisting of pressure data, volume data, flow rate data, temperature data, electrogram data, chemical analyte data, activity data, and accelerometer data.

* * * * *